United States Patent [19] [11] 4,304,906
Kang et al. [45] Dec. 8, 1981

[54] HETEROPOLYSACCHARIDE S-84

[75] Inventors: Kenneth S. Kang, LaJolla; George T. Veeder, San Diego, both of Calif.

[73] Assignee: Merck & Co., Inc., Rahway, N.J.

[21] Appl. No.: 77,241

[22] Filed: Sep. 19, 1979

[51] Int. Cl.³ .......................... C07H 3/06; C08B 37/00
[52] U.S. Cl. .................................... 536/114; 149/21; 260/112 R; 252/8.5 R; 252/315; 252/352; 435/101; 435/104; 536/1; 536/119
[58] Field of Search ........................... 536/1, 114, 119; 435/101, 104

[56] References Cited
U.S. PATENT DOCUMENTS 3,711,462  1/1973  Abdo ........................................ 536/1
3,878,195  4/1975  Taillie et al. ............................. 536/1
3,923,782  12/1975 Finn et al. ................................ 536/1
4,146,705  3/1979  Knutson, Jr. ............................ 536/1

Primary Examiner—Johnnie R. Brown
Attorney, Agent, or Firm—Gabriel Lopez; Hesna J. Pfeiffer

[57] ABSTRACT

The new heteropolysaccharide S-84, prepared by fermentation of an unnamed Pseudomonas species, ATCC 31562 has valuable properties as a thickening, suspending and stabilizing agent in aqueous systems. It is especially useful in formulating explosive gels. Its chemical composition is within the following weight ranges of sugars: 8–15% glucuronic acid; 40–50% glucose; 35–45% mannose; 5–15% rhamnose; and 3–9% arabinose; it also contains 1–5% acetyl and 2–7% pyruvate groups.

2 Claims, No Drawings

HETEROPOLYSACCHARIDE S-84

BACKGROUND OF THE INVENTION

Compound S-84 may be prepared by fermentation of a suitable nutrient medium with a hitherto undescribed organism, based on extensive taxonomic studies, which is an unnamed Pseudomonas species. An unrestricted permanent deposit of this organism employed in making our heteropolysaccharide was made with the American Type Culture Collection on Sept. 10, 1979 under Accession No. ATCC 31562.

The following considerations make the assignment of a new Pseudomonas species justified and necessary.

DESCRIPTION OF THE STRAIN

A. Characteristics of Colonial Morphology

Small yellow colonies appear on nutrient agar in two days at 30° C. The diameter reaches about 1.2–1.8 mm after 4 days' incubation. The colonies are round, smooth, convex, and opaque. Slimy properties are not significant. No membranous texture is observed.

On YM agar, small, mucoid, yellow colonies appear in two days at 30° C. with the diameter reaching 2–3.8 mm after 4 days' incubation. The colonies are round, smooth, convex, and translucent. Umbonate forms with concentric rings may develop with prolonged incubation. No membranous texture is observed.

B. Characteristics of Cell Morphology

Strain S-84 is a gram-negative rod-shaped bacterium. On nutrient agar (2 days old) the average size of the cell is about 0.5–0.6 by 1.2–1.6 μm; one end of the cell is tapered. Very long cells (about 8–10 μm long) may appear and cells may not be stained evenly because vacuole-like structures may appear with prolonged incubation.

On YM agar (2 days old) the average cell size is 0.6 by 1.6–2.0 μm and one end of the cell is often tapered. Curved rods are often seen and vacuole-like structures also appear. Occasionally, very long, thin rods may be seen. Accumulation of PHB was not observed. Palisade aggregation is common on YM agar.

Flagella stains (modified silver nitrate method) showed that the strain was polar monotrichously flagellated.

C. Physiological and Biochemical Characteristics

Cytochrome-oxidase is weak or negative; catalase positive. Organism is capable of growth at 30° C., but not at 37° C. Tolerance to 3.0% NaCl, but not to 6.5% NaCl. Growth at pH's between 5 and 1.

Aerobic acid but not gas was produced from the following carbohydrates:

| | |
|---|---|
| L-Arabinose | Mannose |
| D-Glucose | Maltose |
| Fructose | Mannitol |
| Galactose | |

Acid was *not* produced from the following carbohydrates:

| | |
|---|---|
| D-Xylose | Adonitol |
| L-Rhamnose | Dulcitol |
| Lactose | Sorbitol |
| Melibiose | Salicin |
| Sucrose | Inulin |
| Trehalose | Inositol |
| Raffinose | |

No acid reduction was observed in litmus milk, but peptonization was seen. Ammonium was produced, but not $H_2S$. ADH, ODC, and LDC were negative; PDA was positive. Urease, indole, MR, VP, and Simmon's citrate tests were negative. Nitrate and nitrite not reduced. Phosphatase and 3-Ketolactose tests were negative. Gelatin, casein, starch, Tween 80, esculin, and egg yolk were hydrolyzed. No survival at 60° C. for 30 minutes.

The organism grows on EMB, MacConkey, and Tellurite agar, but not on SS or Pseudosel agar. Nile Blue and Congo Red dyes were not absorbed.

| D. Antibiotic Susceptibility Test | |
|---|---|
| The strain S-84 is susceptible to the following antibiotics | |
| Kanamycin | 30 μg |
| Neomycin | 30 μg |
| Chlortetracycline | 5 μg |
| Colistin | 10 μg |
| Novobiocin | 30 μg |
| Erythromycin | 15 μg |
| Polymyxin B | 300 units |
| Tetracycline | 30 μg |
| Gentamicin | 10 μg |

S-84 is *not* susceptible to the following antibiotics:

| | |
|---|---|
| Penicillin | 10 units |
| Carbenicillin | 50 μg |

| E. Nutritional Characteristics | | |
|---|---|---|
| D-Xylose | Acetate | Pyruvate |
| D-Arabinose | Heptanoate | Mannitol |
| D-Glucose | Pelargonate | n-propanol |
| D-Mannose | Malonate | Phenyl-acetate |
| D-Galactose | Succinate | Quinate |
| D-Fructose | Fumarate | L-α-Alanine |
| Sucrose | L-Malate | L-Aspartate |
| Trehalose | DL-Tartrate | L-Histidine |
| Maltose | DL-β-Hydroxy-butyrate | L-Proline |
| Cellobiose | Glycellate | L-Tyrosine |
| Starch | Citrate | α-Keto-glutarate |

F. Identification by API System

The strain S-84 was not identified by either the API or OXI/FERM tube systems. This suggests that the organism could not be isolated from a clinical source.

G. Identification

The strain S-84 is a gram-negative, rod-shaped organism with polar flagellum. It is aerobic; cytochrome-oxidase is weak or negative, and catalase positive. According to the definition of Bergey's Manual (8th edition) this organism is a member of the genus Pseudomonas.

TABLE 1

Biochemical and Other Miscellaneous Tests Employed for the Strain S-84

| Test | Result | Test | Result |
|---|---|---|---|
| Oxidase: Kovacs's | + | Hydrolysis of: | |
| Pathotech | − | Gelatin | + |
| | | Casein | + |
| Catalase | + | Starch | + |
| OF medium: Oxidative | + | Tween 80 | + |
| Fermentative | − | Pectin | − |
| Gas from glucose | − | Alginate | NT |
| $H_2S$ production: TSI | − | Cellulose | − |
| from cystine | + | Chitin | − |
| Ammonium from peptone | + | DNA | NT |
| β-Galactosidase (ONPG) | − | Esculin | +/− |
| Arginine dihydrolase | − | | |
| Lysine decarboxylase | − | Growth on various media: | |
| Ornithine decarboxylase | − | EMB agar | + |
| Tryptophan deaminase | NT | MacConkey agar | + |
| Phenylalanine deaminase | + | SS agar | − |
| Urease | − | Mannitol salt agar | − |
| Indole | − | TCBS agar | − |
| MR test | − | Tinsdale tellurite | . |
| VP test | − | blood agar | + |
| Nitrate reduction | − | Pseudosel agar | − |
| Nitrite reduction | − | | |
| Denitrification | − | Pigment production: | |
| $N_2$- fixation | | King A medium | − |
| Growth in Burk's medium | + | King B medium | − |
| Nitrogenase activity | NT | | |
| Malonate (oxidation) | − | Dye reaction: | |
| Phosphatase | + | Congo red | − |
| Haemolysis (sheep blood) | NT | Nite blue | − |
| Litmus milk: acid, reduction only | − | | |
| 3-ketolactose production | − | | |
| Survival at 60° C. for 30 min. | − | | |
| TSI: Slant | color no change | | |
| Butt | color no change | | |
| Gas | − | | |
| Egg Yolk Reaction | + | | |

+ = Positive
− = Negative
NT = Not tested

FERMENTATION CONDITIONS:

Heteropolysaccharide S-84 is produced during the aerobic fermentation of suitable aqueous nutrient media under controlled conditions via the inoculation with the organism of the unnamed Pseudomonas species. The media are usual media, containing source of carbon, nitrogen and inorganic salts.

In general, carbohydrates (for example, glucose, fructose, maltose, sucrose, xylose, mannitol, corn syrup, starch and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 4% by weight of the medium. Preferably 3% glucose is used. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted tht the media described in the examples are merely illustrative of the wide variety of media which may be employed, and are not intended to be limitative.

One important media characteristic is that when strain S-84 is grown under low $CA^{++}$ conditions, i.e., in deionized water, or an aqueous system having less than 200 ppm $Ca^{++}$ ions, the resultant gum is readily soluble in solutions without gelling.

The fermentation is carried out at temperatures ranging from about 25° C. to 35° C.; however, for optimum results it is preferable to conduct the fermentation at temperatures of from about 28° C. to 32° C. The pH of the nutrient media for growing the Pseudomonas culture and producing the polysaccharide S-84 can vary from about 6 to 8, preferably 6.5 to 7.5.

Although the polysaccharide S-84 is produced by both surface and submerged culture, it is preferred to carry out the fermentation in the submerged state.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1 ∝ 2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-84 is particularly suited for the preparation of large quantities.

The product is recovered from the fermentation medium by precipitation with a suitable alcohol, such as isopropanol.

HETEROPOLYSACCHARIDE S-84

The heteropolysaccharide produced by an unnamed Pseudomonas species is composed principally of carbohydrate with 1-5% acetyl groups as the O-glycosidically linked ester, and 2-7% pyruvate groups.

The carbohydrate portion of the S-84 polysaccharide contains 8-15% glucuronic acid; 40-50% glucose; 35-45% mannose; 5-15% rhamnose; and 3-9% arabinose.

The acetyl content of 1-5% was determined by treating a 0.2% aqueous solution of S-84 gum with an alkaline, hydroxylamine reagent followed by treatment with an acidic ferric chloride reagent [S. Hestrin (1949) *J. Biol. Chem.* 180 pp. 249-261].

The neutral sugars of polysaccharide S-84 were determined by dissolving ten mg. of the product in 2 ml 2N $H_2SO_4$, and the mixture is heated at 100° C. for 4 hours. The resulting solution is cooled, neutralized with barium hydroxide and the pH is brought to 5-6 with solid carbon dioxide. The resulting precipitate of barium sulfide is removed by centrifugation and the supernatent is concentrated to a syrup under reduced pressure. The sugars in the hydrolysate are tentatively identified by gas-liquid chromatography of their aldononitrile acetate derivatives on a Hewlett-Packard Model 5750 chromatograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) *Carbohydr. Res.* 27 pp. 464-467].

The various neutral sugars of the polysaccharides were also characterized by use of descending paper chromatography on Whatman No. 1 chromatography paper using as the solvent the upper layer of pyridine-:ethyl acetate-water (2:5:5). Chromatograms were stained using silver nitrate dip and acid analine phthalate spray reagent. Component sugars were identified by co-chromatography with sugar standards and by the specific-color reaction with the analine phthalate reagent.

The glucuronic acid content of the polysaccharide was determined by two separate methods. In one method the sample was decarboxylated with 19% hydrochloric acid and the liberated carbon dioxide was trapped in standard sodium hydroxide and determined by back titration [B. L. Browning (1967) *Methods of Wood Chemistry* II, pp. 632-633] and by the carbazole colorimetric method [T. Bitter and H. M. Muir (1962) *Anal. Biochem.* 4 pp. 330-334].

Paper electrophoresis was used for the separation and tentative identification of the glucuronic acid present in the neutralized acid hydrolysate described above. Aliquots of this and known glucuronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the glucuronic acids being separated.

The polysaccharide S-84 imparts viscosity to an aqueous medium when dissolved in water in low concentrations. Because of this, its sensitivity to shear and over all rheology, it is useful as a thickening, suspending, emulsifying, stabilizing, lubricating, film-forming, or binding agent, especially in aqueous systems. In particular, it has uses in the following applications or products: adhesives, wall-joint cements, water-retentive grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrated and flowable pesticides and herbicides, tobacco binders, water-based inks, lithographic fountain solutions, leather finishes, hydro-mulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressings, dry mixes, icings, and glazes, syrups, puddings, farinaceous foods, canned and retorted foods, and bakery fillings.

A particularly valuable utility is in the field of explosive gel formation. More detailed examples illustrating this preferred use are found, infra.

Although S-84 gum possesses a general viscosity-imparting property, its particular profile of solution properties is a distinctive characteristic which enables it to be distinguished over other heteropolysaccharides. An outline of these distinctive properties follows.

Briefly, the gum shows:
(1) excellent heat stability, i.e., only a 12% loss in viscosity when held at 80° C. for 2 hrs;
(2) excellent salt response with the product viscosity increasing in the presence of KCl;
(3) good alkaline stability in a very harsh accelerated test (80° C. for 2 hrs with 15% NaOH);
(4) good suspending ability as evidenced by a WYU of 31 dynes/$cm^2$;
(5) good film formation.

A further study of the heat stability of this product showed that only 28% of its original viscosity was lost when autoclaved at 121° C. and 15 psi for 15 for minutes.

The gum's properties of good viscosity in brine (KCl and NaCl), and seawater, good alkali and heat stability, a constant viscosity over pH ranges 1.5 to 12.1, and good shear stability, make it especially suitable for industrial applications such as explosive gel compositions.

1. Viscosity and Shear
   A. Brookfield
   1. 1.0%
    60 rpm 800 cPs
    6 rpm 4700 cPs
    Spindle No. 3
   2. 0.1% (UL adapter)[a] 13 cPs
   3. 0.5% Wells-Brookfield
    @ 9.6 sec$^{-1}$ 243 cPs
   B. Shear[b]
   1. n @ 1.92 sec$^{-1}$ 4480 cPs
   2. n @ 9.6 sec$^{-1}$ 1050 cPs
   3. n @ 76.8 sec$^{-1}$ 176 cPs
   4. n @ 384 sec$^{-1}$ 48 cPs
   5. n @ $384^2$ sec$^{-1}$ 48 cPs
   6. n @ 9.6 sec$^{-1}$ 973 cPs
   C. 40° F. Storage
    920 cPs, No. 3 spindle @ 60 rpm; gel-like; very chunky, non-continuous flow; increase of 15% viscosity above ambient temperature viscosity.
2. Acid, Base, Heat Stability
   A. Stability
   1. Acetic acid plus heat
    a. initial n: 900 cPs
    b. final n: 540 cPs
    c. % change: −40%
   2. 10% HCl plus heat
    a. initial n: 845 cPs
    b. final n: total loss cPs
    c. % change: total loss %
   3. 15% NaOH plus heat
    a. initial n: 998 cPs
    b. final n: 691 cPs
    c. % change: −31%
   4. Heat only
    a. initial n: 998 cPs
    b. final n: 883 cPs
    c. % change: −12%
   B. pH Effect
   1. 5% Acetic Acid 2.96 pH 885 cPs[c]
   2. 5% NH$_4$OH 11.23 pH 947 cPs[c]
3. Salt and Dye Compatibility
   A. Salt
   1. CaCl$_2$ (saturated) Compatible
   2. Amm. polyphosphate Precipitate
   3. 60% NH$_4$NO$_3$ Compatible
   4. 1% Al$_2$(S0$_4$)$_3$ . 18H$_2$O Compatible
   5. 1% CaCl$_2$ . 2H$_2$O Compatible
   6. 1% KCl Compatible
   7. 0.1% KCl 998 cPs[c]
   8. 2.5% KCl 1360 cPs[c]
   B. Dyes
   1. Milling Green Compatible
   2. Methylene Blue Precipitate
4. Texture/Flow Properties
   Medium viscosity gum; slightly chunky flow; gel-like; not gummy to the touch.
5. Synergism and Enzymes[c]

|  | 1% n | 0 hr n of mixture | 2 hr n of mixture |
|---|---|---|---|
| A. Guar | 1797 cPs | 217 cPs | 1254 cPs |
| B. H.P. Guar | 1754 cPs | 1126 cPs | 909 cPs |
| C. CMC | 832 cPs | 589 cPs | 269 cPs |
| D. HEC | 550 cPs | 410 cPs | 760 cPs |
| E. | 1050 cPs | | |

|  | Expected Viscosity | Synergism |
|---|---|---|
| A. Guar | 1375 cPs | None |
| B. H.P. Guar | 1350 cPs | None |
| C. CMC | 1010 cPs | None |
| D. HEC | 760 cPs | None |

6. Milk Reactivity
   A. Dispersion: Excellent
   B. Whey Off: First day.
   C. Other observations:
7. Film Formation
   Excellent film formed; plastic; good tensile strength; very clear film.

[a]Viscosity measured on a Brookfield Model LVF at 6 rpm with the No. 1 spindle and a UL adapter.
[b]All measurements made on a Wells-Brookfield microviscometer Model RVT-c/p.
[c]Viscosity measured on a Wells-Brookfield microviscometer Model RVT-c/p at 9.6 sec$^{-1}$.

EXAMPLE 1

Fermentation Procedure for Producing Heteropolysaccharide S-84

A. Culture Maintenance

The unnamed Pseudomonas organism, ATCC 31562, grows quite well on E-1 medium agar, with good colonial morphology. E-1medium is as follows (solid medium add 1.5% agar):

| K$_2$HPO$_4$ | 0.5% |
|---|---|
| NH$_4$NO$_3$ | 0.09% |
| Promosoy | 0.05% |
| MgSO$_4$ . 7H$_2$O | 0.01% |
| Tap water | |
| Carbon source (3% hydrolyzed starch) | |

The incubation temperature is 30° C., and for 72 hours.

B. Seed Preparation

Flasks seeds are prepared in YM broth incubated at 30° C. for 24 hours, then used as a seed for E-1 medium, which is incubated at 30° C. for 72 hours. A small scale fermentation was also done on E-1 contains 3% glucose instead of starch, yielding a product with slightly higher product viscosity.

C. Final Fermentor Medium

The isolate has been scaled-up in fermentors of three sizes (14L, 20L, and 70L) and the results are shown in Table 2. In each case the final fermentor medium was E-1 plus 1ppm Fe$^{++}$ and 3% glucose as the carbon source. Seeds were started in YM broth and allowed to incubate for 48 hours at 30° C. on a gyrotary shaker. For the 14L fermentors, such a YM seed was used to start five flasks containing E-1 medium and these were used at 24 hours to inoculate a 14L fermentor. For the larger fermentors, two 48-hour old YM broth seeds were used to inoculate a one-gallon fermentor containing final fermentor medium. These one-gallon fermentors were allowed to go 48–72 hours prior to using them to seed the larger fermentors.

The fermentors were run at 30° C. The starting air and agitation rates for each fermentor were as follows:
(1) 14L 3L/M, 400 rpm
(2) 20L 10L/M, 300 rpm
(3) 70L 20L/M, 300 rpm The aeration rate remained constant throughout the fermentation period. The agitation was increased during the fermentation as needed to obtain good mixing. The phosphate level in the medium for the 14L, 20L, and 70L fermentors was decreased to 0.05% and the pH was controlled at 6.5-7.5 with the automatic addition of 25% KOH. The results of these scale-ups are shown in the following table:

| SCALE-UP CHARACTERISTICS OF S-84 | | | | | |
|---|---|---|---|---|---|
| Fermentor | Age (hrs) | Beer Vis. (cP) | RCS (%) | Yield (%) | 1% Vis. (cP) |
| 14L | 23 | 20 | ND | 0.20 | |
| | 92 | 520 | 1.36 | 0.78 | |
| | 114 | 920 | 1.06 | 0.99 | |
| | 145 | 1260 | 0.33 | 1.08 | |
| | 161 | 1420 | 0.17 | 1.11 | 800 |
| 20L | 44 | 255 | 2.47 | 0.59 | |
| | 66 | 1400 | 1.65 | 0.98 | |
| | 87 | 1850 | 0.80 | 1.48 | |
| | 116 | 1875 | 0.10 | 1.92 | 660 |
| 70L | 20 | 30 | 2.50 | 0.17 | |
| | 39 | 75 | ND | 0.20 | |
| | 91 | 440 | 1.10 | 0.88 | 410 |
| | 119 | 1850 | 0.10 | 1.59 | |

D. Recovery

Recovery was by precipitation with 2-3 volumes of 99% isopropanol. When pasteurized, conditions are heating at 167° F. for 10-15 minutes prior to recovery E. Drying Product can be recovered after drying at 50°-55° C. for about one hour in a forced-air tray dryer.

The product prepared in this example analyzes as follows: 10.4% glucuronic acid by decarboxylation; 13.1% glucuronic acid by colorimetric analysis; 3.5 % pyruvate; 2.9% acetyl, 45% glucose; 39% mannose; 10% rhamnose; 6% arabinose; and 7.2% protein.

It is further characterized as a medium-viscosity (800 cPs) anionic gum. Its viscosity increased 15% upon overnight's refrigeration. It has good heat stability losing only 12% viscosity at 80° C. for two hours. Further testing indicated a 28% viscosity loss upon autoclaving at 121° C. for 15 minutes. It is very KCL-reactive as its viscosity increased by 25% in the presence of 2.5% KCl. It formed a plastic film with good tensile strength. It has a working yield value of 31.5 (1% solution in DI water).

EXAMPLE 2

Low-Calcium S-84

Low calcium S-84 can be prepared as in Example 1, except using deionized water, 1 ppm $Fe^{++}$ and 2 ppm $Ca^{++}$. Small amounts of trace elements such as vitamins or metals can be added for good growth. The low calcium product has excellent heat stability.

EXAMPLE 2

Formulations

Aqueous explosive slurries are generally composed of oxidizer salts selected from various ammonium and alkali metal nitrates and perchlorates, alkaline metal nitrates and perchlorates and may also contain insoluble fuels, sensitizers, thickeners, and cross-linking agents. Guar gum is usually the primary thickener due to cost, solubility, and other considerations; however, the guar gum is not stable in the hot oxidizer solutions used and serious viscosity losses and impaired water resistance of the cross-linked explosive slurries occurs. U.S. Pat. No. 3,728,173 teaches the use of guar gum plus xanthan gum for imparting long term stability and U.S. Pat. No. 3,867,320 teaches that the addition of xanthan gum improves water resistance of thickened slurries.

Cross-linking agents are preferably employed with the thickening agent in order to further stabilize dispersion of fuels, suspend insolubles, and especially to stabilize slurries in boreholes containing water, i.e., provide water resistance. Small amounts of chromates are the most commonly used cross-linking agents although many others have been used to gel the slurries to produce the aforementioned effects. It is, therefore, a requirement of the thickener that it cross-links easily or at least provides water resistance by not interfering with the guar cross-linking.

While xanthan gum is used in combination with guar to improve stability and water resistance, it has been found that polysaccharide S-84 is more efficient than xanthan gum in promoting water resistance, has good solubility in hot concentrated ammonium nitrate solutions, and does not interfere with cross-linking by chromates.

Water resistance tests were performed by preparing 500 g of a 70% ammonium nitrate solution in water at 70° C. and dissolving a blend of 1.0 g of guar gum plus 0.5 g xanthan gum or polysaccharide S-84 for two hours. The solution was placed in a stoppered bottle to which was added 0.25 ml of a 20% sodium nitrite solution and 1.0 ml of a 50% sodium dichromate solution. 0.05% thiourea was also added to control reaction of the nitrite gassing solution. The hot mixture was shaken vigorously for 15 seconds then poured into one liter of ambient temperature water. At that point gelation had begun and gas bubbles had started to form with the gel. The gels were evaluated for water resistance by observing the gel surface for streamers of gel containing gas which rise from the surface. Good water resistance is shown by a continuous surface with few streamers as the gas is entrapped within the gel matrix and not permitted to escape. Observations were made after one hour and after 24 hours with the following results:

| | Thickener | Water Resistance |
|---|---|---|
| (1) | 1.5 g guar | Poor after 24 hours. |
| (2) | 1.0 g guar 0.5 g xanthan gum | Good. |
| (3) | 1.0 g guar 0.5 g S-84 | Good. |
| (4) | 1.0 g guar 0.4 g S-84 | Good. |
| (5) | 1.25 g guar 0.25 g xanthan gum | Fair. Starts to break up slightly after 24 hours. |
| (6) | 1.25 g guar 0.25 g S-84 | Good. Smooth, more continuous surface then xanthan gum after 24 hours. |

S-84 can be used to improve water resistance of explosive slurries and is more efficient than xanthan gum at lower concentrations. Generally, S-84 is more useful in explosive slurries at 0.05-0.2%, optionally in combination with guar gum at 0.05-0.5% (all weights based on total weight). Gums can be dry blended and dissolved directly in oxidizer solution, or added separately.

What is claimed is:

1. Heteropolysaccharide S-84, prepared by fermentation under controlled conditions of culture ATCC 31562, a Pseudomonas species; said S-84 containing 8-15% glucuronic acid, and the neutral sugars: mannose, glucose, rhamnose and arabinose in the approximate molar ratios of 35-45%; 40-50%; 5-15%; and 3-9%, respectively; 1-5% O-acetyl groups; 2-7% pyruvate groups and having the following physical properties: a 1% viscosity (measured on Brookfield Spindle No. 3) at 60 rpm of 800 cPs, at 6 rpm of 4,700 cPs; the gum being incompatible (precipitating) in ammonium polyphosphate; and compatible in $CaCl_2$ (saturated); 60% $NH_4NO_3$; 1% $Al_2(SO_4)_3.18H_2O$; 1% $CaCl_2.2H_2O$, and 1% KCl; and having viscosity measurements on a Wells-Brookfield microviscometer Model RVT-cP at 9.6 $sec^{-1}$ in 0.1% KCl of 998 cPs and in 2.5 KCl of 1,360 cPs.

2. The heteropolysaccharide of claim 1, which contains less than 200 ppm Ca.

* * * * *